US00PP32117P2

(12) United States Plant Patent
Eveleens et al.

(10) Patent No.: US PP32,117 P2
(45) Date of Patent: Aug. 25, 2020

(54) ***HYDRANGEA* PLANT NAMED 'HOKOMALURE'**

(50) Latin Name: *Hydrangea macrophylla*
Varietal Denomination: Hokomalure

(71) Applicants: Horteve Breeding BV, Aalsmeer (NL); Kolster Holding BV, Boskoop (NL)

(72) Inventors: Cornelis Pieter Eveleens, Aalsmeer (NL); Peter Rudolf Kolster, Boskoop (NL)

(73) Assignees: HORTEVE BREEDING BV, Aalsmeer (NL), part interest; KOLSTER HOLDING BV, Boskoop (NL), part interest ( * ) Notice: Subject to any disclaimer, the term of this patent is extended or adjusted under 35 U.S.C. 154(b) by 0 days.

(21) Appl. No.: 16/602,077

(22) Filed: Aug. 1, 2019

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Hydrangea macrophylla* plant named 'Hokomalure' that is characterized by its leaves that are very dark brown-red in color, its sterile flowers that are picotee colored (yellow and pink) when young and mature to pink, its sterile sepal edges that are crenate, its upright plant habit, and its suitability as a potted plant.

2 Drawing Sheets

Botanical classification: *Hydrangea macrophylla.*
Varietal denomination: 'Hokomalure'.

CROSS REFERENCE TO RELATED APPLICATIONS

This application is related to U.S. Plant Patents for a plant derived from the same breeding program that are entitled *Hydrangea* Plant Named 'Hortfire' (U.S. Pat. No. 29,058) and *Hydrangea* Plant Named 'Horthamp' (U.S. Plant Pat. No. 29,005).

BACKGROUND OF THE INVENTION

The present invention relates to a new and distinct cultivar of *Hydrangea macrophylla* and will be referred to hereafter by its cultivar name, 'Hokomalure'. 'Hokomalure' represents a new bigleaf *Hydrangea*, a perennial shrub grown for landscape use and as a potted plant.

'Hokomalure' derived from an ongoing controlled breeding program directed by the Inventors. An objective of the breeding program included developing a new cultivar of *Hydrangea* with dark leaves, a floriferous blooming habit and other desirable traits.

'Hokomalure' arose from a controlled cross made by one of the Inventors in Boskoop, The Netherlands in June of 2012 between *Hydrangea* 'Sweet Fantasy' (not patented) as the female parent and an unnamed and unpatented proprietary plant in the Inventor's breeding program (reference no. 07-120-08) as the male parent. 'Hokomalure' was selected as a single unique plant from amongst the resulting seedlings in August of 2014.

Asexual propagation of the new cultivar was first accomplished by stem cuttings by one of the Inventors in August of 2014 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomalure' as a unique cultivar of *Hydrangea macrophylla.*

1. 'Hokomalure' exhibits leaves that are very dark brown-red in color.
2. 'Hokomalure' exhibits sterile flowers with sepal edges that are crenate.
3. 'Hokomalure' exhibits an upright plant habit.
4. 'Hokomalure' exhibits suitability as a potted plant.
5. 'Hokomalure' exhibits picotee colored sterile flowers when young (yellow and pink) that mature to pink.

The female parent of 'Hokomalure' differs from 'Hokomalure' in having sterile flower sepals that are pink with dark pink stripes and smooth margins and in having green leaves. The male parent of 'Hokomalure' differs from 'Hokomalure' in having leaves that are lighter red in color and sterile flower sepals that are more picotee in color. 'Hokomalure' can be most closely compared to the *Hydrangea macrophylla* cultivars 'Hortfire' and 'Horthamp'. 'Hortfire' is similar to 'Hokomalure' in having sterile flower sepals that are picotee colored and in having with deeper crenate margins, lighter color leaves and a more floriferous blooming habit. 'Horthamp' is similar to 'Hokomalure' in having sterile flower sepals that are picotee colored, dark color leaves and an upright growing habit. 'Horthamp' differs from 'Hokomalure' in having sterile flower sepals with a more intense flower color and smooth margins, leaves that are lighter in color, and a more floriferous blooming habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1). Disclosures include but may not be limited by a website description (a site that does not offer plants for sale) by Plants Nouveau.

BRIEF DESCRIPTION OF THE DRAWINGS

The accompanying colored photographs illustrate the overall appearance and distinct characteristics of the new *Hydrangea*. The photographs were taken of a two-year-old plant of 'Hokomalure' as grown in a greenhouse in a 17-cm container in Boskoop, The Netherlands.

The photograph in FIG. 1 provides a side view of the plant habit of 'Hokomalure' in bloom.

Figure 1:
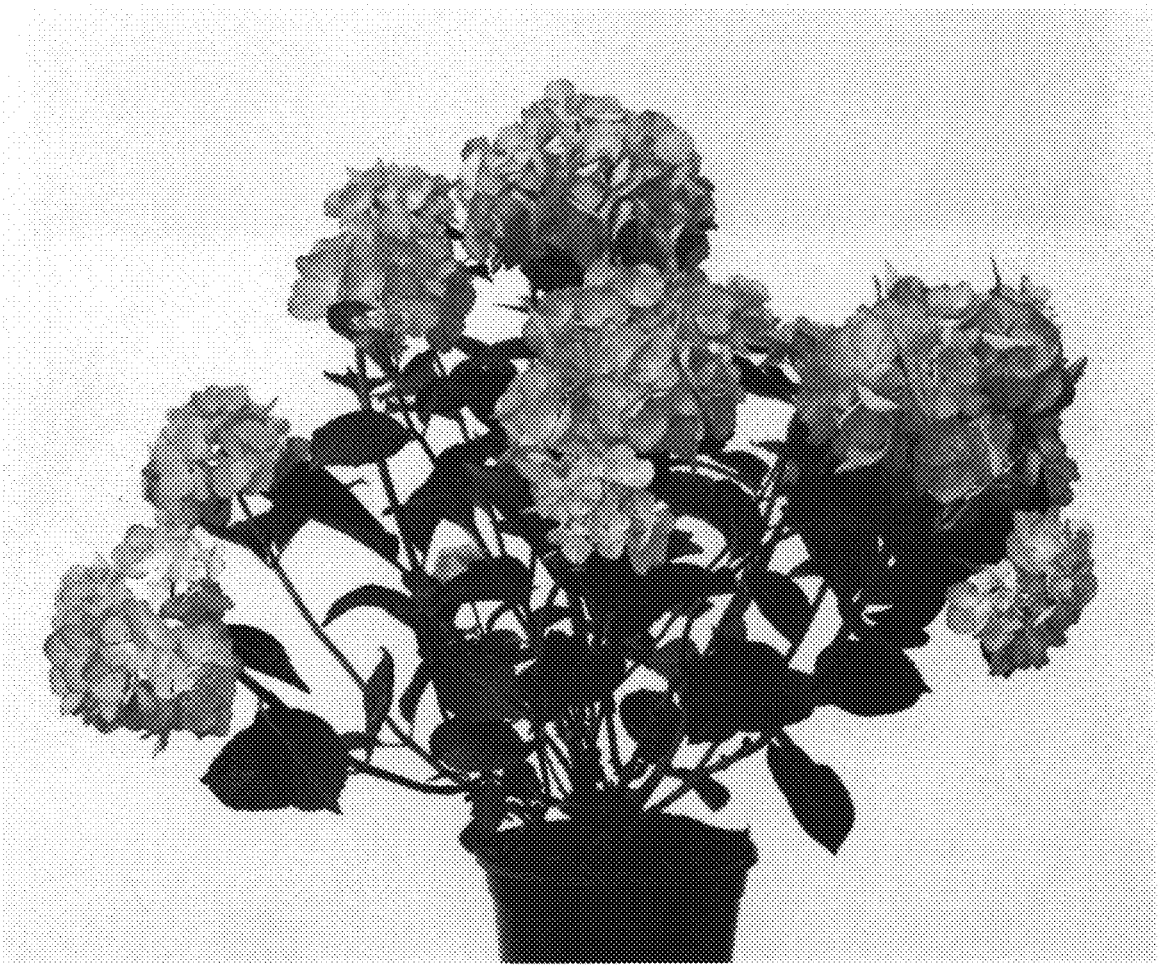
Figure 2:
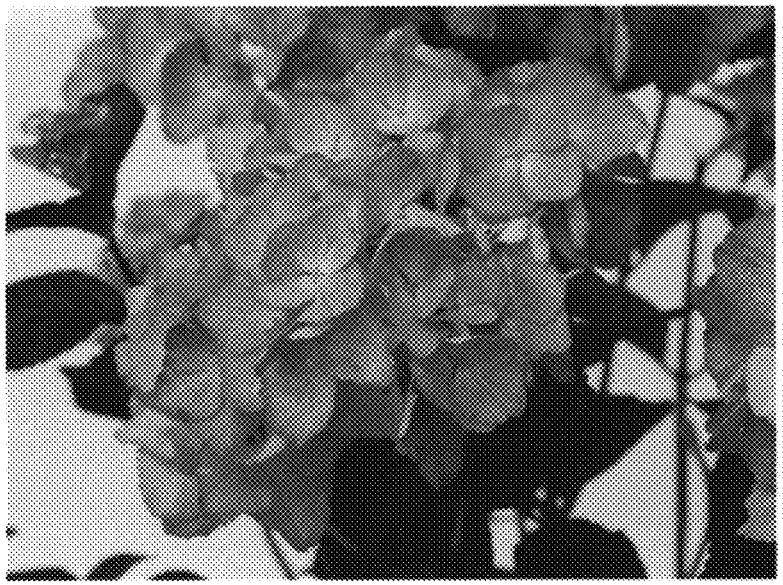

The photograph in FIG. 2 provides a close-up view of a fully open inflorescence of 'Hokomalure'.

Figure 3:
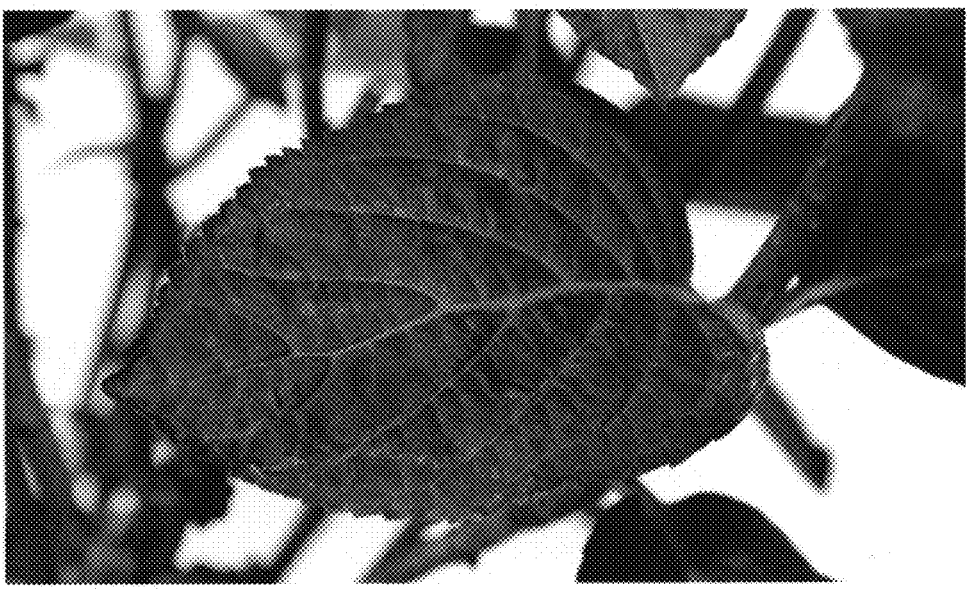

The photograph in FIG. 3 provides a close-up view of the foliage of 'Hokomalure'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'Hokomalure' as grown in a greenhouse in 17-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

- *Blooming period.*—Late spring to late summer with flowers showy at least for 2 months in the Netherlands.
- *Plant type.*—Deciduous shrub, mophead type *Hydrangea.*
- *Plant habit.*—Broad spreading, upright.
- *Height and spread.*—An average of 53 cm in in height and 60.5 cm in spread as grown in a 13-cm container, reaches 1 m in height and spread as a 3-year-old plant in the landscape.
- *Hardiness.*—At least in U.S.D.A. Zones 5 to 9.
- *Diseases and pests.*—No susceptibility and resistance to diseases or pests has been observed.
- *Root description.*—Fine and fibrous, 161C in color.
- *Propagation.*—Stem cuttings.
- *Root development.*—An average of 6 weeks for root initiation with a young rooted plant produced in an average of 18 weeks.
- *Growth rate and vigor.*—Moderate.

Stem description:

- *Stem shape.*—Rounded.
- *Stem strength.*—Strong.
- *Stem color.*—Young; 144A, mature; 144A, internodes tinged with 187A, old bark; 199B to 199D.
- *Stem size.*—An average of 23.8 cm in length (excluding inflorescence) and 7 mm in diameter.
- *Stem surface.*—Stems are very sparsely covered with thin soft hairs that are an average of 1.5 mm in length and too small to measure color also moderately covered with lenticels that are an average of 2.5 mm in length and 1 mm in diameter, N186C in color.
- *Stem aspect.*—Average angle of 35° from vertical.
- *Internode length.*—An average of 6.5 cm.
- *Branching.*—Freely branching with an average of 20 lateral branches.

Foliage description:

- *Leaf shape.*—Broad ovate.
- *Leaf arrangement.*—Opposite.
- *Leaf division.*—Simple.
- *Leaf base.*—Short attenuate to truncate.
- *Leaf apex.*—Apiculate.
- *Leaf margins.*—Coarsely dentate to serrate.
- *Leaf venation.*—Pinnate, color; color upper surface 144A, lower surface 148A, changing to 146A at the base.
- *Leaf size.*—An average of 10 cm in length and 7 cm in width.
- *Leaf attachment.*—Petiolate.
- *Leaf number.*—An average of 8 to 10 per lateral stem.
- *Leaf surface.*—Both surfaces; smooth and moderately rugose.
- *Leaf color.*—Young foliage; upper surface NN137B, tinged 203A towards the tip, lower surface 147B, tinged 200A toward the tip, mature foliage; upper surface 147A, strongly flushed with 200A and 203B, lower surface between 147B and 191A.
- *Petioles.*—An average of 1 cm in length and 4 mm in diameter, upper surface color 147C, lower surface color 143B, both surfaces are smooth and slightly glossy.

Inflorescence description:

- *Inflorescence type.*—Terminal panicle, flattened mophead comprised of sterile flowers above fertile flowers.
- *Lastingness of inflorescence.*—Sterile flowers; persistent for an average of 6 weeks, fertile flowers; self-cleaning, an average of 5 days.
- *Inflorescence number.*—One per lateral stem.
- *Inflorescence size.*—An average of 12.7 cm in height and 18.2 cm in diameter.
- *Flower number.*—An average of 75 sterile flowers and 20 fertile flowers per panicle.
- *Flower fragrance.*—None.
- *Flower aspect.*—Sterile flowers; upright to slightly drooping, fertile flowers; upright.
- *Flower size.*—Sterile flowers; an average of 6.7 cm in diameter and 1.7 cm in depth, fertile flowers; an average of 5 mm in diameter and depth.
- *Flower type.*—Rotate.
- *Flower buds.*—Sterile flowers; an average of 8 mm in length and 1.1 cm in diameter, cup-shaped, 145C in color and margined 61D, fertile flowers; an average of 5 mm in length and 4 mm in diameter, broad obovate in shape, 59D in color and changing to 63D at the base.

*Peduncles.*—Strong, flattened oval in shape, an average of 3 cm in length and 2.5 mm in width on primary peduncles and secondary peduncles 2 cm in length and 2.3 mm in width, 159C to 159D in color, surface dull and densely pubescent surface covered with thin pubescence an average of 0.2 mm in length and too small to measure color.

*Pedicels.*—Sterile flowers; held primarily at an average angle of 25° from vertical, an average of 2.3 cm in length and 2 mm in diameter, moderately strong strength, 159C to 159D in color, surface matte and moderately covered with thin pubescence an average of 0.2 mm in length and too small to measure color, moderately covered with lenticels that are 180A in color, fertile flowers; held at an average angle of 15° from vertical, an average of 3.5 mm in length and 1 mm in diameter, moderate strength, 150D in color, surface matte and moderately covered with thin pubescent hairs an average of 0.2 mm in length and too small to measure color.

*Petals.*—Sterile flowers; an average of 4, rotate, cruciform in arrangement, broadly acute apex, broadly cuneate base, entire margins, broadly ovate to moderately to strongly concave in shape, average of 2.5 mm in length and 1.5 mm in width, both surfaces; glabrous and matte, color when opening and fully open upper and lower surface 62C, color not fading, fertile flowers; an average 5, rotate in arrangement, ovate and concave in shape, entire margin, acute apex, cuneate base, an average of 3.5 mm in length and 1.5 mm in width, upper and lower surface glabrous and matte, color upper and lower surface when opening and fully open 59D, changing to 63D at the base.

*Sepals.*—Sterile flowers; 4, rotate, emarginate apex, broadly cuneate base, entire to moderately undulate margins, broad ovate to reniform in shape, an average of 3.7 cm in length and 4.2 cm in width, upper and lower surface glabrous and matte, color; when opening upper surface 63B, changing to 150D at the base, when opening lower surface 150D, changing to 59D at the margins, when fully open upper surface 63B, fading to 59C and 60B, veined 146D, when fully open lower surface 63C, changing to 63B at the margins, fading to 181C to 181D, veined 146C to 146D, fertile flowers; an average of 5, ovate in shape, entire margin, acute apex, 2 mm in length, 1.5 cm width, and broadly cuneate base, both surfaces are glabrous and matte, color; upper and lower surface when opening 144B, upper and lower surface when fully open 150D with tip 63D.

Reproductive organs:

*Gynoecium.*—Sterile flowers; 2 to 3 pistils, an average of 1 mm in length, stigma; club-shaped and 144D in color, style; 0.75 mm in length, 144C in color, ovary is 144D in color, fertile flowers; an average of 2 to 3 pistils, an average of 1.5 mm in length, stigma; club-shaped and NN155C in color, style; 0.5 mm in length and 150D in color, ovary is 150D in color.

*Androecium.*—Sterile flowers; an average of 8 stamens, filaments; an average of 1 mm in length and NN155D in color, anthers; broad oblong in shape, an average of 0.5 mm in length and 155D in color, pollen; low in quantity, 155B in color, fertile flowers; an average of 8 stamens, filaments; an average of 3 mm in length and NN155D in color, anthers; broad oblong in shape, an average of 0.5 mm in length and 155D in color, pollen; low in quantity and 155B in color.

*Fruit and seed.*—None observed to date.

It is claimed:

1. A new and distinct cultivar of *Hydrangea* plant named 'Hokomalure' substantially as herein illustrated and described.

* * * * *